April 23, 1940. V. A. SILVERA Plant Pat. 380

PEAR TREE

Filed Aug. 28, 1939

INVENTOR
Victor A. Silvera
John A. Naismith
ATTORNEY

Patented Apr. 23, 1940

Plant Pat. 380

UNITED STATES PATENT OFFICE

380

PEAR TREE

Victor A. Silvera, near Milpitas, Calif.

Application August 28, 1939, Serial No. 292,236

1 Claim. (Cl. 47—62)

My invention relates particularly to a sport of that variety of pear known throughout the world generally as the "Hardy" pear, and more particularly known as the "Beurre Hardy."

This Hardy variety of pear has become so well known among growers and shippers that reference to its physical characteristics is not deemed necessary, other than to point out that the almost unvarying uniformity in the greenish or greenish-yellow coloring of the fruit is relieved only by a faint blush where the fruit is exposed to the direct action of the sun's rays or to intense light.

It is a well known fact that the ultimate purchaser of any article of merchandise is influenced greatly by the color of that article, an attractive color materially enhancing its sales value. The unattractive coloring of the well-known Hardy pear of commerce, as above indicated, is a real hindrance to its successful exploitation.

As hereinafter more fully set forth I have developed a pear that is substantially identical with the Hardy pear of commerce except as to color, which is a reddish brown, thereby rendering it exceedingly desirable to prospective purchasers.

Figure 1:
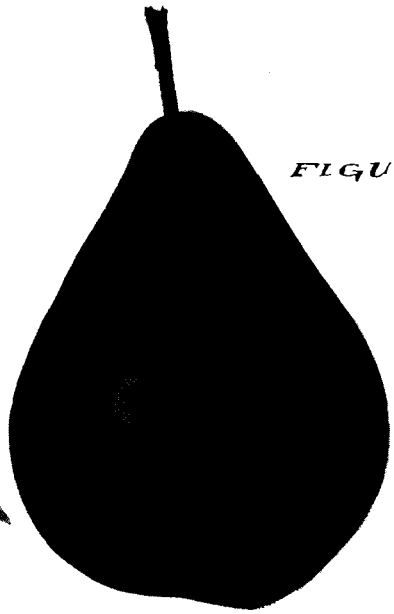
Figure 1 shows an oil color drawing of my improved pear.

The fruit having the special characteristic color shown in Figure 1 was first discovered growing on a bud sport of a Beurre Hardy tree, one of a large number comprising an orchard. There were three pears on this sport, all characterized by the new color shown, and all growing to maturity.

The year following the discovery of the first three pears the sport bore no fruit, therefore I cut off the end of the sport just beyond a spur and scored the sport deeply on the trunk side of the spur. I also scored the surrounding limbs in order to force an abundant flow of sap to the spur and so secure a robust budding spur.

As a result of the above described operation a spur was grown that provided me with five buds, and these buds were grafted into five quince seedlings, and all grew into sturdy branches.

Taking new wood from the branches above referred to I grafted these into Easter Beurre pear trees, and I also took buds from those branches and bud-grafted them into Beurre Hardy pear trees, and have found that the new color remains constant throughout each succeeding generation in each case.

Figure 2:
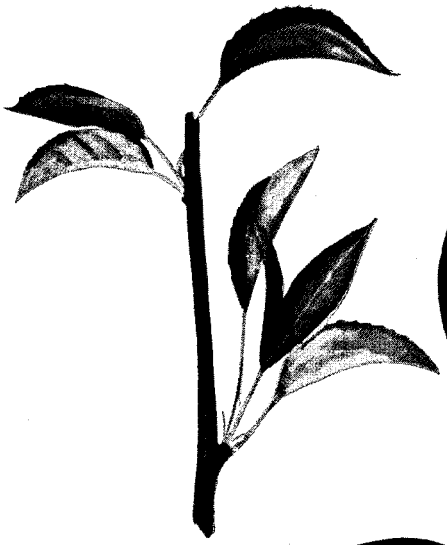
Figure 2 shows an oil color drawing of a portion of a new-growth shoot from a branch bearing my improved pear.

In watching the development of the plants from the five buds above described I observed that the new growth appearing each year was colored as shown in Figure 2, and that this coloring appeared uniformly in all new shoots on these and all subsequent graftings of the new variety.

Figure 3:
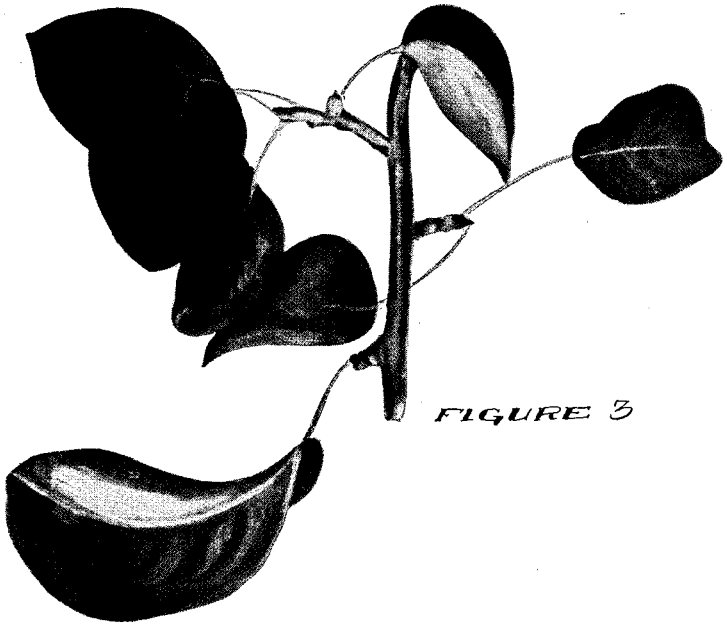
Figure 3 shows an oil color drawing of a portion of an old branch bearing my improved pear.

It is now evident that the novel coloring shown and described is a fixed characteristic of the tree because the old wood is tinged with it as shown in Figure 3 and the old leaves assume a darker green, demonstrating the fact that the entire plant is modified as to color, the new color being decidedly conspicuous in the new growth, but more modified as the age of the wood increases.

This new pear tree characterized by the novel coloring shown has not been tested elsewhere than on the premises of the originator, nor has it been named, characterized or described in print.

I claim:

A new and distinct variety of Beurre Hardy type pear tree characterized particularly by the dark reddish brown color of its fruit and new wood, and the brown tinge of its older wood, and its dark green foliage.

VICTOR A. SILVERA.